United States Patent [19]
Hajishoreh

[11] Patent Number: 5,458,580
[45] Date of Patent: Oct. 17, 1995

[54] SYRINGE APPARATUS

[76] Inventor: Kaveh-Karimi Hajishoreh, 5501 Newcastle Ave., No. 62, Encino, Calif. 91310

[21] Appl. No.: 215,184

[22] Filed: Mar. 21, 1994

Related U.S. Application Data

[63] Continuation-in-part of Ser. No. 34,244, Mar. 22, 1993.

[51] Int. Cl.$^6$ .............................. A61M 5/00; A61M 5/31
[52] U.S. Cl. ............................................ 604/240; 604/110
[58] Field of Search ..................... 604/110, 195, 604/232–235, 240, 242, 243; 128/763–765

[56] References Cited

U.S. PATENT DOCUMENTS

| | | | |
|---|---|---|---|
| 2,505,307 | 4/1950 | Smith | 128/218 |
| 2,505,308 | 4/1950 | Smith | 128/218 |
| 2,561,233 | 7/1951 | Ryan et al. | 128/218 |
| 2,672,868 | 3/1954 | Hickey | 128/218 |
| 3,141,583 | 7/1964 | Mapel et al. | 222/309 |
| 4,457,712 | 7/1984 | Dragan | 433/90 |
| 4,784,607 | 11/1988 | Francois | 433/90 |
| 4,950,163 | 8/1990 | Zimble | 433/215 |
| 4,985,020 | 1/1991 | Kasuya | 604/192 |

FOREIGN PATENT DOCUMENTS

| | | |
|---|---|---|
| 671078 | 12/1929 | France . |
| 1364845 | 5/1964 | France . |

*Primary Examiner*—C. Fred Rosenbaum
*Assistant Examiner*—Frank Wilkens, III
*Attorney, Agent, or Firm*—Dick and Harris

[57] ABSTRACT

An improved syringe apparatus for use with interchangeable, disposable medicinal ampoules is provided with an advantageous mechanism for facilitated, one-handed operation in the ejection of a spent ampoule. The improved construction also includes a needle ejector projection for one-handed ejection of the used, disposable needle assembly. An improved cap apparatus for covering the needle assembly is also provided.

9 Claims, 4 Drawing Sheets

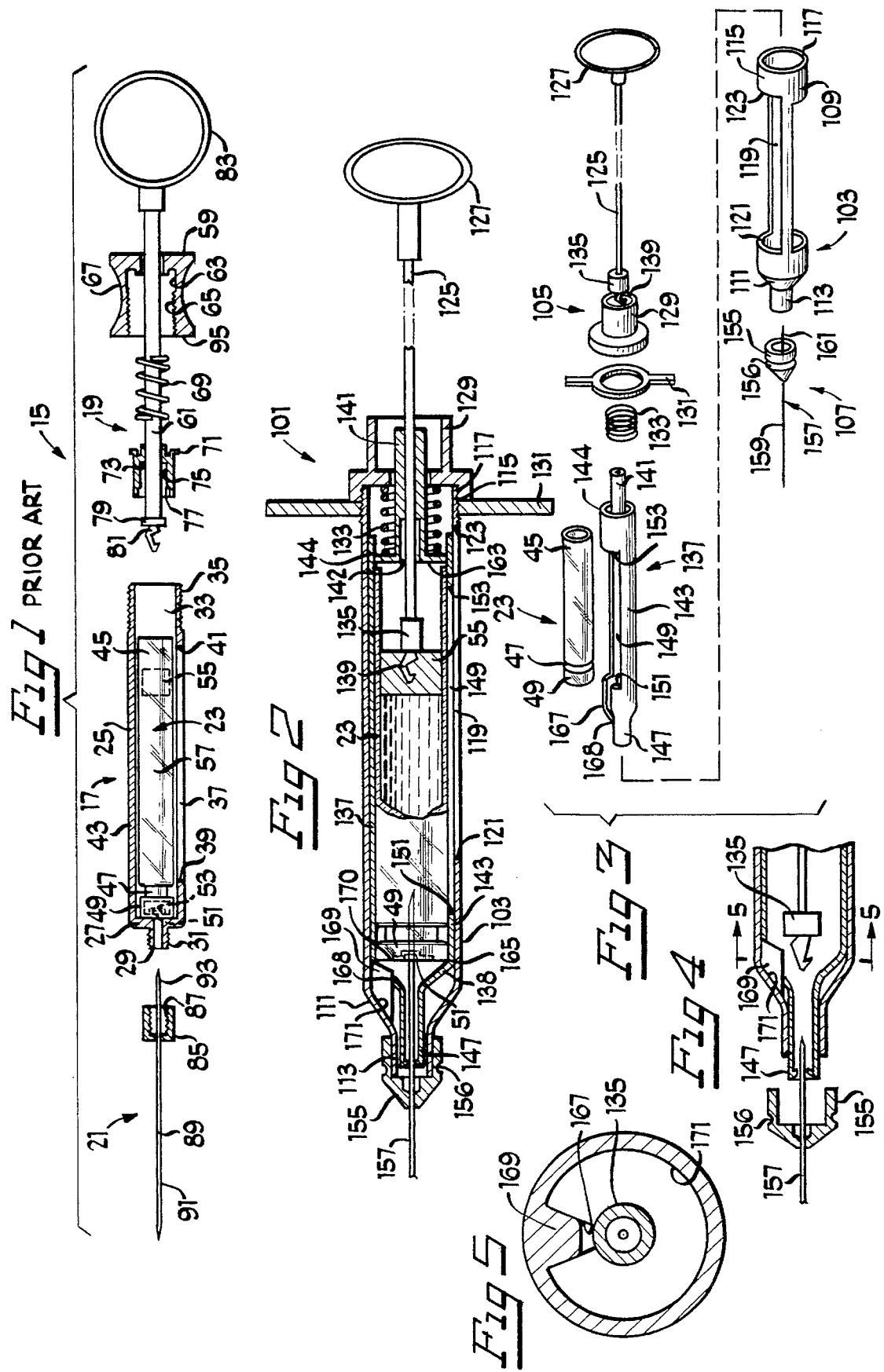

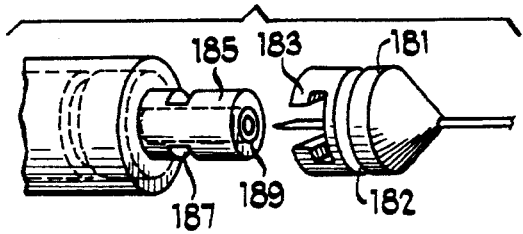
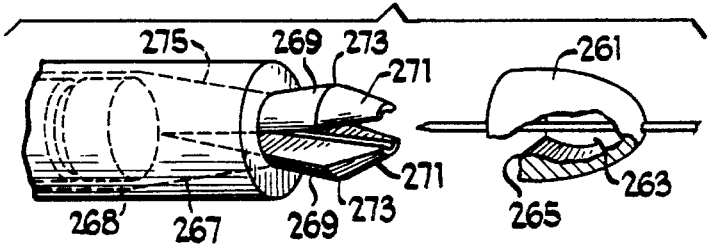
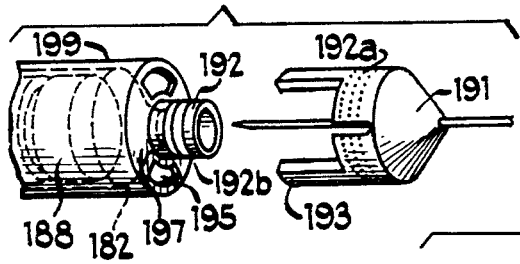
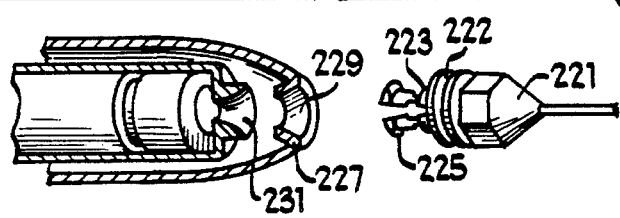
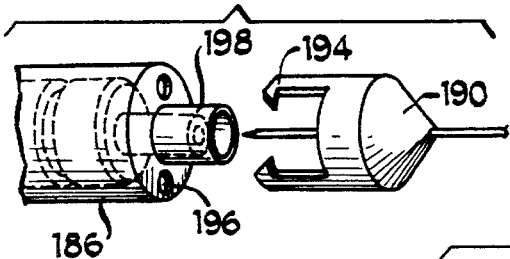
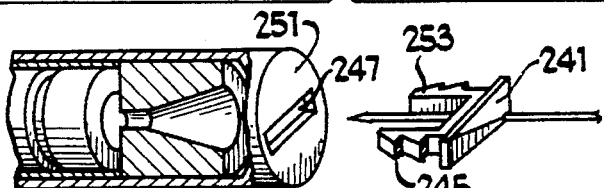
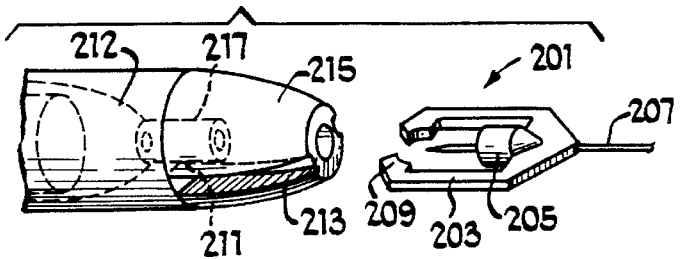
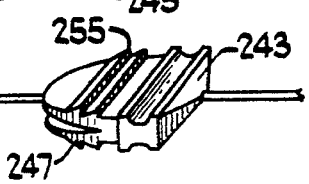

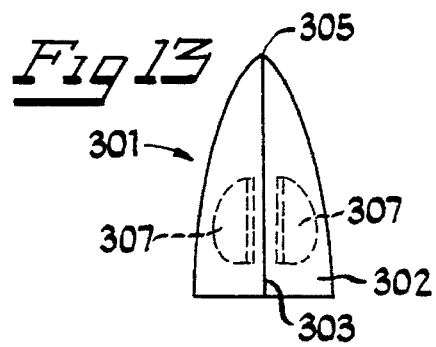
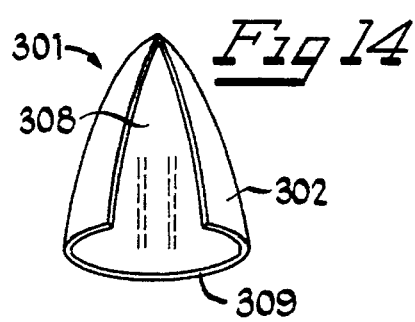
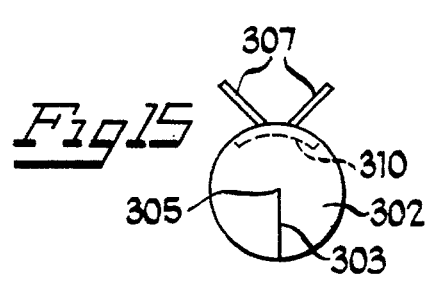
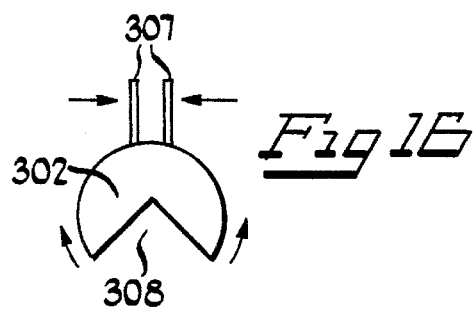
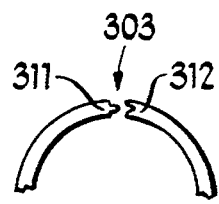
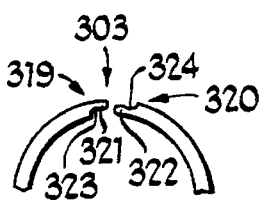
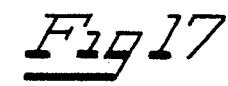
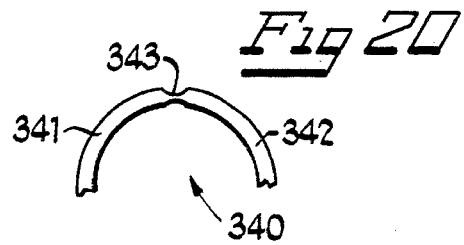

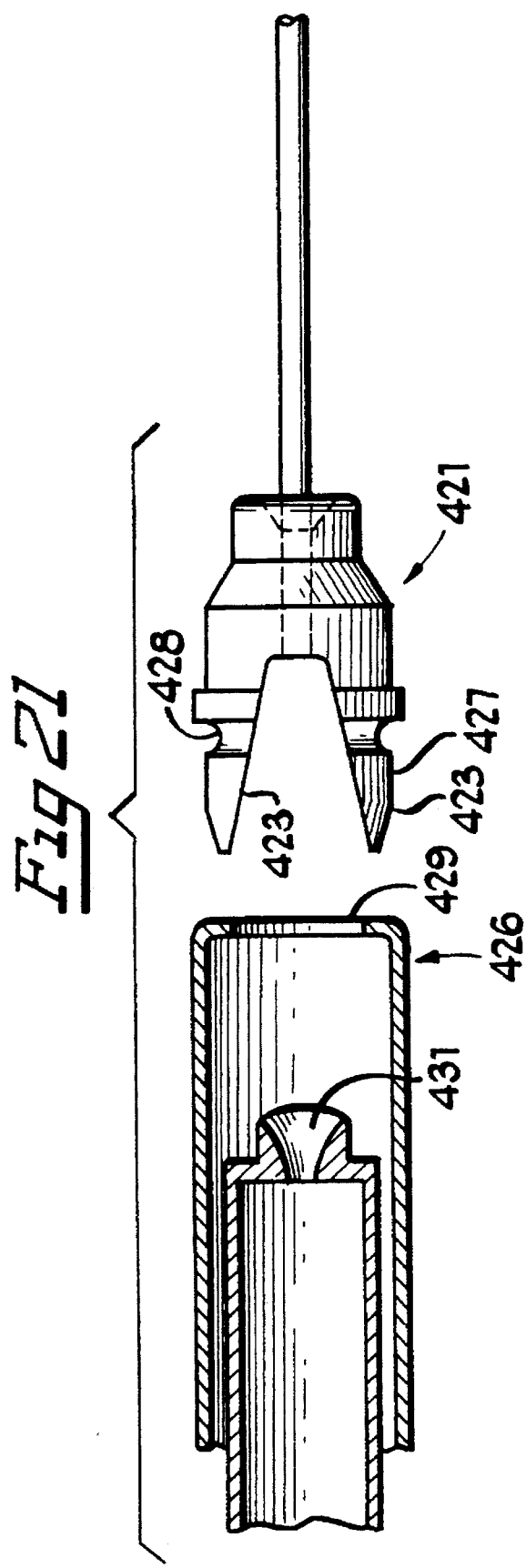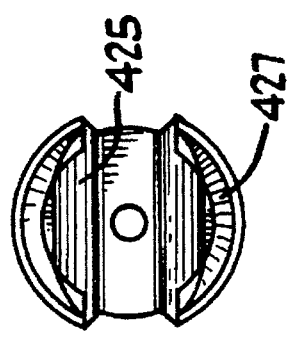

SYRINGE APPARATUS

This is a continuation-in-part of U.S. patent application Ser. No. 08/034,244, filed Mar. 22, 1993, now currently allowed.

The present invention is directed to syringes for hypodermic needles, and in particular to syringes which are configured to enable the use of prepared ampoules, which ampoules contain a measured amount of medicinal or other liquid, and which are inserted into the syringe, and removed and discarded after use. Such ampoules typically are formed as a glass cylinder having a puncturable seal at one end. A rubber stopper closes the other end to retain the liquid in the ampoule. The rubber stopper is configured to act as a plunger piston, capable of being pushed along the length of the cylinder, so long as the liquid is capable of escaping from the other end of the ampoule via a needle piercing the puncturable seal.

A typical prior art syringe, which employs such exchangeable ampoules, comprises a syringe body, which may be a hollow substantially cylindrical shell, which has openings at its forward and rearward ends, as well as at least one lateral opening. A plunger assembly is attachable to the rearward end of the syringe body. The plunger assembly usually includes an outer collar which may be internally threaded, so as to screw onto external threads on the rearward end of the syringe body. A plunger shaft is centered within the collar, and capable of sliding axially relative to the collar. On the forward end of the plunger shaft a hook, which emanates from a disk having a diameter slightly greater than that of the plunger shaft, is provided to engage the plunger piston in the ampoule. At the rearward end of the plunger shaft, a thumb ring or other gripping device is provided to enable both forward and rearward force to be applied by the operator.

An inner collar is also slidingly arranged around the plunger shaft, and constrained to move, only between the disk on the plunger shaft, and the outer collar, The inner collar has a diameter less than the interior diameter of the syringe body, but equal or greater than that of the ampoule, and is arranged with the plunger shaft, so that when the plunger shaft is moved forward, the inner collar can remain stationary, pressed against the ampoule by a slightly compressed spring situated in a central well in the outer collar. The inner collar also has a central well, so that when the plunger shaft is drawn rearward, away from the ampoule, the disk and hook are capable of receding into the central well, below the level of the outer rim of the collar, before the disk actually engages the inner collar, and upon continued rearward force, begins to pull the inner collar in the rearward direction.

At the forward end of the syringe body, a coupling for receiving a needle assembly is provided. A typical needle assembly is a cap member, through which a hollow needle member projects in both direction, with sharp beveled openings at both ends of the needle member. The coupling is usually a cylindrical projection having external threading thereon. The cap member will have corresponding internal threading. An aperture, wide enough for the rearward end of the needle member to pass, is provided in the center of the coupling, and leads to the interior of the syringe body. Present needle assembly constructions are intended to be disposable after one use, to prevent the inadvertent transmission of disease, and eliminate the cost and effort incurred by sterilization procedures.

When the syringe is in an unloaded, unstressed condition, the distance between the inner collar of the plunger assembly and the inner surface of the forward end of the syringe body is less than the length of the typical medicinal ampoule. To enable insertion of the ampoule, the plunger shaft must be drawn rearward against the force of the spring in the central well of the outer collar. After insertion of the ampoule, and release of the plunger shaft, the inner collar, under the bias of the spring, presses the ampoule against the forward inner surface of the syringe body, to help maintain it securely in place. In addition, as the ampoule is pressed forward, the seal comes up against the interior end of the needle member, which pierces the seal and extends into the ampoule, enabling the liquid therein to be driven out, upon pressing of the plunger shaft.

As an additional measure of security, for example, to prevent lateral movement of the ampoule during the process of locating the needle or during the process of pressing the plunger shaft, the lateral opening in the side of the syringe body is wide enough, but not long enough to enable the ampoule to be directly inserted, when the syringe is in the initial unloaded configuration. However, when the plunger shaft is pulled rearwardly enough to move the inner collar, the ampoule may be pivoted and inserted through the aperture. In the typical configuration, the ampoule must be inserted rear end first. When the plunger shaft is released, the inner collar pushes the ampoule forward, until the front end of the ampoule is substantially surrounded by the syringe body and the ampoule cannot be dislodged.

Once the ampoule has been loaded, the operator pushes on the thumb ring, to embed the hook into the plunger piston, bringing the disk flush against the plunger piston. The operator then executes the injection procedure. Once finished, the operator withdraws the needle and prepares to remove the ampoule by drawing back on the thumb ring, to pull the plunger shaft out of the ampoule. Further rearward force on the thumb ring will draw the disk, against the force of the spring, into the central well of the inner collar, ultimately to move the inner collar rearward, away from the ampoule. A problem arises, however, in that once the plunger shaft has been withdrawn from "inside" the ampoule, the ampoule cannot be readily removed from within the syringe body. The seal at the forward end of the ampoule exerts sufficient force on the interior needle end that external rearward force must be applied to back the ampoule off of the interior needle end and enable the ampoule to be removed from the syringe body.

While this may not be a significant problem in the event that only a single ampoule is to be used for a single patient, as the needle assembly might be removed first, it is frequently the case that multiple ampoules/injections will be desired or necessary for a single patient. For the operator to have to employ two-handed effort to replace each ampoule is inefficient, slows the treatment procedure, and increases the potential for injury, contamination, and so on.

Accordingly, it would be desirable to provide a syringe which is adapted to use interchangeable, disposable ampoules, with a means for assuring alignment of the ampoule with the loading/unloading aperture, to enable assured ejection of the used ampoule with only one-handed manipulation required.

The previously described prior art syringe also employs a needle assembly in which the needle is supported and centered by a needle retainer member which is screwed onto a coupling projecting from the front of the syringe body.

It would be desirable to provide a syringe apparatus in which the needle assembly is configured to be removed more easily. For the very same health and sanitation reasons for which the needle assemblies are being made disposable, it is desirable as well to provide a needle assembly which does not require the use of two hands in order to affect its separation from the syringe body. Even more desirable would be a way to eject the spent needle assembly without having to actually touch the needle assembly.

An additional consideration is that the needle tip should be sheathed prior to mounting upon the syringe body, to prevent accidental injury to the operator or patient, and also to maintain the needle in a sterile condition as long as possible, but also after use, again to prevent injury, and to also preclude possible transmission of disease from the contaminated needle assembly. Conventional cap apparatus must applied to the needle assembly by approaching the assembly directly toward the exposed needle point, which presents an undesirable risk of injury.

It is, accordingly, a further object of the invention to provide for an improved needle assembly construction which provides for the facilitated removal of the spent needle assembly.

Yet another object of the invention is to provide a needle assembly construction which does not require the use of two hands to effect the ejection of the spent needle assembly.

A further object of the invention is to provide a construction which permits the ejection of the needle assembly without requiring the operator to actually touch the spent needle.

A still further object of the invention is to provide an improved cap apparatus which enables facilitated covering of the needle assembly prior to and after usage, with reduced risk of injury and transmission of disease.

These and other objects of the invention will become apparent in light of the present specification, claims and drawings.

SUMMARY OF THE INVENTION

The present invention is a syringe apparatus of the type which utilizes interchangeable ampoules, each ampoule being preloaded with a charge and having a breachable seal at a front end thereof and further having a plunger piston arranged integrally within the ampoule substantially adjacent a rear end thereof to enclose and seal the charge within the ampoule.

The syringe apparatus comprises a substantially hollow syringe body having a longitudinal axis, a forward end having a first forward aperture therein, a rearward end, and at least one lateral aperture operably configured to substantially receive therethrough one of said interchangeable ampoules into said hollow syringe body. Plunger assembly means are operably positionable in cooperation with the rearward end of the syringe body and positionable to cooperate with the plunger piston, when the ampoule is received with the substantially hollow syringe body, to enable the plunger piston to be driven toward the forward end of the syringe body, to, in turn, enable the charge to be driven out of the ampoule, when the seal of the ampoule has been breached and held open. The plunger assembly means is further operably configured to releasably maintain the ampoule within the syringe body in substantial non-alignment with the lateral aperture in the syringe body so as to preclude inadvertent escape of the ampoule from within the syringe body.

Means for facilitating removal of the ampoule from the substantially hollow syringe body after the charge has been substantially driven from the ampoule, by enabling the ampoule to be selectively positionable in substantial alignment with the lateral aperture in the syringe body through application of external pushing force onto the ampoule, independently of the plunger piston, to enable substantially single-handed removal of the ampoule from the substantially hollow syringe body, are operably associated with the plunger assembly means.

The plunger assembly means comprises a plunger shaft member operably configured for reciprocable movement parallel to the longitudinal axis, substantially within the hollow syringe body. Means are also provided, which are operably configured for pushing the plunger piston toward the forward end of the syringe body, and are operably disposed upon a forward end of the plunger shaft.

The means for facilitating removal of the ampoule from the substantially hollow syringe body comprises an ampoule carrier frame means, operably associated with the plunger assembly means, and configured to be received within said syringe body for movement therein parallel to said longitudinal axis. The ampoule carrier frame means is configured to receive and substantially axially surround one of the interchangeable ampoules so that the ampoule carrier frame means and the ampoule may be constrained to move together along the longitudinal axis of the syringe body. The ampoule carrier frame means is further operably configured for limited axial movement relative to the plunger shaft member, so that when the plunger shaft member is moved along the longitudinal axis, away from the forward end of the syringe body, the ampoule carrier frame means will subsequently be constrained to move away from the forward end of the syringe body, and toward a position of said substantial alignment with the lateral aperture.

A coupling is disposed upon the forward end of the syringe body, which substantially surrounds the first forward aperture and upon which the cap-like needle retainer member is configured to fit. In a preferred embodiment of the invention, the syringe apparatus further comprises needle assembly means including a cap-like needle retainer member, which is operably configured to releasably and removably fit over and affix to the coupling, in operable juxtaposition to the first forward aperture. A substantially hollow needle member is operably supported by and passes substantially centrally through the cap-like needle retainer member. The needle member has an exterior end, which is operably configured for insertion into a patient to enable delivery of the charge, and has an interior end, which is operably configured to pierce the breachable seal of the ampoule to enable release of the charge from the ampoule through the needle member. Means are also provided for releasably retaining the needle retainer member upon the forward end of the syringe body in the operable juxtaposition with the first forward aperture, together with means for enabling substantially single-handed ejection of the needle assembly means from the syringe body.

The means for enabling substantially single-handed ejection of the needle assembly means from the syringe body, once the ampoule has been ejected from the syringe body, comprises, in a preferred embodiment, a needle ejector projection, operably arranged upon a forward end of the ampoule carrier frame, and having a diameter less than that of the first forward aperture, so that the needle ejector projection may extend through the first forward aperture and press against said needle retainer member, when the plunger shaft member is pushed forward, so as to push the needle assembly means off of the forward end of the syringe body.

In a preferred embodiment of the invention, the syringe apparatus further comprises means for selectively precluding ejection of the needle assembly means from the syringe body, which, in a preferred embodiment of the invention, further comprises at least one obstruction member, which operably emanates inwardly from an interior surface of the substantially hollow syringe body, substantially adjacent the forward end thereof. At least one corresponding obstruction groove is operably disposed upon a forward end of the ampoule carrier frame. The at least one obstruction member and the at least one obstruction groove are aligned upon assembly of the syringe apparatus. When one of the ampoules in positioned within the ampoule carrier frame, the obstruction member abuts a front face of the ampoule, and prevents the ampoule carrier frame from being positioned sufficiently forward to enable the needle ejector projection to push the needle assembly off of the syringe body. When no ampoule is present within the ampoule carrier frame, however, the ampoule carrier frame is capable of being moved sufficiently forward to enable the needle ejector projection to push the needle retainer member off of the coupling to accomplish the ejection of the needle assembly means.

In a preferred embodiment of the invention, the needle retainer member includes at least one flexible catch member operably configured to releasably engage a corresponding at least one notch operably disposed upon the coupling, so as to grip the coupling, with the at least one catch member being configured to bend, and release the at least one notch, upon application of a predetermined amount of force by the needle ejector projection upon the needle retainer member, to enable ejection of the needle assembly means.

In an alternative preferred embodiment of the invention, the needle retainer member is provided with at least one rearwardly projecting member, which is operably configured to be received by a corresponding at least one alignment aperture in the forward end of the syringe body, when the needle retainer member is in the operable juxtaposition to the first forward aperture. The at least one rearwardly projecting member is biased to also project inwardly toward the longitudinal axis and frictionally grip the syringe body. The at least one rearwardly projecting member further includes at least one flexible catch member operably configured to releasably engage a corresponding at least one alignment aperture in the forward end of the syringe body, so as to grip the coupling, so that when the at least one rearwardly projecting member is received within the at least one alignment aperture, the needle retainer member will be releasably retained upon the forward end of the syringe body. The at least one rearwardly projecting member is also configured to flexibly yield upon application of a predetermined amount of force by the needle ejector projection upon the needle retainer member, to enable ejection of the needle assembly means.

In an alternative embodiment, a substantially blunt forward shoulder on the ampoule carrier frame member, rather than a needle ejector projection, is configured to press against the rearwardly projecting prongs to force the needle retainer member off of the forward end of the syringe body.

In a further alternative embodiment of the invention, the needle retainer member is also provided with at least one rearwardly projecting member, which is operably configured to be received by a corresponding at least one alignment aperture in the forward end of the syringe body, when the needle retainer member is in the operable juxtaposition to the first forward aperture. The at least one rearwardly projecting member is biased to extend outwardly away from the longitudinal axis and frictionally grip the syringe body, so that when the at least one rearwardly projecting member is received within the first forward aperture, the needle retainer member will be releasably retained upon the forward end of the syringe body. The needle ejector projection will have a concave forward surface thereon, so that upon application of a predetermined amount of force by the needle ejector projection upon the needle retainer member, the concave surface will force the at least one rearwardly projecting member inwardly toward the longitudinal axis to enable ejection of the needle assembly means.

In a still further alternative embodiment of the invention, the needle retainer member is provided with a rearward-facing aperture having a first diameter, and an interior chamber having a diameter greater than the first diameter. In this embodiment, the needle ejector projection comprises at least one forwardly projecting member, operably configured to extend through the first forward aperture in the syringe body, and into the interior chamber of the needle retainer member. The at least one forwardly projecting member is biased to extend outwardly away from the longitudinal axis when the ampoule carrier frame is in a forward position within the syringe body, and grip the needle retainer member by pressing outwardly against an inner surface of the interior chamber. The at least one forwardly projecting member is configured to move inwardly toward the longitudinal axis when the ampoule carrier frame is in a rearward position within the syringe body, so as to release the needle retainer member.

The present invention also comprises an improved cap apparatus for use with a syringe of the type utilizing interchangeable, disposable needle assemblies, in which each needle assembly includes a needle retainer member and a needle member. The cap apparatus is a substantially elongated cap member, having a front end, a rear end and a longitudinal axis, which is operably configured to substantially surround the needle member and at least a portion of the needle retainer member. The cap member has a selectively openable and closable lateral aperture therein which is capable of permitting receipt of the needle member and the portion of the needle retainer member through it. Means are provided for enabling selective opening of the lateral aperture by the operator.

In a preferred embodiment of the invention, the lateral aperture is a substantially longitudinally extending slit formed by mating longitudinally extending edges in the cap member which extend from the rear end to the front end. The means for enabling selective opening of the lateral aperture comprises at least one pair of tab members which operably extend substantially radially out from the cap member, symmetrically about a position substantially opposite from the slit. The at least one pair of tab members are operably affixed to the cap member so that upon exertion of pressure upon radially outer edges of the tab members to force the radially outer edges of the tab members toward one another, the pressure causes the cap member to distort, spreading apart the longitudinally extending mating edges.

In a preferred embodiment of the invention, a needle retainer member of a needle assembly is provided with a circumferentially extending groove, and a circumferentially extending, inwardly projecting ridge is provided within the cap member which is operably engageable with the circumferentially extending groove to facilitate retention of the cap member upon the needle assembly.

Means for providing a seal along the slit to facilitate protection of the needle assembly, and retention of the cap member upon the needle assembly are also provided. In a preferred embodiment of the invention, the means for providing a seal comprise a ridge operably emanating from one of the slit edges toward the other of the slit edges, and a corresponding groove operably disposed in the other of the slit edges, operably configured to receive the ridge. In an alternative embodiment of the invention, the means for providing a seal comprises corresponding overlapping and interlocking ridges and grooves, operably disposed in each of the slit edges, respectively, so that when the lateral aperture is closed, a ridge from one edge resides in and engages a groove in the corresponding edge.

The cap apparatus may also be provided with means for biasing the cap member into a position wherein the lateral aperture is closed. In a preferred embodiment of the invention, the means for biasing the cap member comprises a resilient member operably arranged within the cap member, substantially adjacent the tab members, and operably configured to bias the edges of the slit toward one another.

The invention further comprises a needle retainer apparatus, for use in combination with a syringe apparatus, of the type having a syringe body having a forward end and a rearward end thereof, and a plunger member operably associated with the syringe body and operably configured for longitudinal movement relative to the syringe body. In particular, the needle retainer apparatus comprises a needle retainer member, operably configured to be releasably affixed to said forward end of said syringe body; and means for releasably affixing said needle retainer member upon said forward end of said syringe body, and for enabling removal of said needle retainer member from said syringe body through extension of force upon said needle retainer member, parallel to said longitudinal axis, in a direction away from said syringe body, operably associated with said needle retainer member and said syringe body.

The means for maintaining said needle retainer member in releasable affixation upon said forward end of said syringe body may be at least one resilient grasping member operably disposed upon a rearward portion of said needle retainer member; and means for releasably engaging said at least one grasping member, operably disposed upon said forward end of said syringe body, such that when said needle retainer member is brought into juxtaposition against said forward end of said syringe body, said at least one resilient grasping member grasps said syringe body to maintain said needle retainer member in operable engagement with said syringe body, and whereupon exertion of a predetermined force against said needle retainer, said at least one grasping member and said means for releasably engaging said at least one grasping member cooperate to enable release of said needle retainer member from said syringe body.

In a preferred embodiment of the invention, the at least one resilient grasping member is a prong member extending rearwardly from said needle retainer member; and has at least one barb member projecting inwardly from said prong member. The means for engaging said at least one grasping member, operably disposed upon said forward end of said syringe body comprises at least one recess in said forward end of said syringe body, operably configured to receive at least one of said at least one prong member and said at least one barb member.

Alternatively, the at least one resilient grasping member comprises a resilient prong member extending rearwardly from said needle retainer member; and at least one barb member projecting outwardly from said prong member, and the means for engaging said at least one grasping member, operably disposed upon said forward end of said syringe body comprises at least one recess in said forward end of said syringe body, operably configured to receive at least one of said at least one prong member and said at least one barb member.

In a further embodiment of the invention, the means for maintaining said needle retainer member in releasable affixation upon said forward end of said syringe body comprises at least one resilient grasping member operably associated with said syringe body, and operably positioned adjacent said forward portion thereof; and means for releasably engaging said at least one grasping member, operably disposed upon said needle retainer member, such that when said needle retainer member is brought into juxtaposition against said forward end of said syringe body, said at least one resilient grasping member grasps said needle retainer member to maintain said needle retainer member in operable engagement with said syringe body, and whereupon exertion of a predetermined force against said needle retainer member, said at least one grasping member and said means for releasably engaging said at least one grasping member cooperate to enable release of said needle retainer member from said syringe body.

In particular, the needle retainer member includes an inner recess having an inner surface and a rearwardly facing opening therein, and said at least one resilient grasping member comprises at least one circumferentially extending ridge emanating radially inwardly from said inner surface of said inner recess. The means for engaging said at least one grasping member, operably disposed upon said forward end of said syringe body comprises at least one circumferentially extending recess in said forward end of said syringe body, operably configured to receive said at least one circumferentially extending ridge emanating radially inwardly from said inner surface of said inner recess.

The invention also comprises means for releasing said needle retainer member from said syringe body, operably associated with said needle retainer member and said plunger member.

BRIEF DESCRIPTION OF THE DRAWINGS

FIG. 1 is a partially exploded elevational view, partly in section, of a prior art syringe apparatus;

FIG. 2 is a side elevational view, partly in section, of an assembled syringe apparatus according to a preferred embodiment of the present invention;

FIG. 3 is an exploded perspective view of a syringe apparatus according to FIG. 2;

FIG. 4 is a side elevational view, in section, showing the structure provided for preventing automatic ejection of the needle assembly;

FIG. 5 is a sectional view of the structure provided for preventing automatic ejection of the needle assembly, taken along line 5—5 of FIG. 4;

FIG. 6 is a perspective view, partly in section, of a needle assembly according to a preferred embodiment of the invention;

FIG. 7 is a perspective view, partly in section, of a needle assembly according to a further preferred embodiment of the invention;

FIG. 8 is a perspective view, partly in section, of a needle assembly according to another preferred embodiment of the invention;

FIG. 9 is a perspective view, partly in section, of a needle assembly according to still another preferred embodiment of the invention;

FIG. 10 is a perspective view, partly in section, of a needle assembly according to still yet another preferred embodiment of the invention;

FIG. 11 is a perspective view, partly in section, of a needle assembly according to a still further preferred embodiment of the invention;

FIG. 12 is a perspective view, partly in section, of a needle assembly according to a yet still further preferred embodiment of the invention;

FIG. 13 is a front elevational view of an improved needle cap apparatus according to the present invention, in its unopened configuration;

FIG. 14 is a front elevational view of the cap apparatus according to FIG. 13, shown in its opened configuration;

FIG. 15 is a top plan view of the cap apparatus according to FIG. 13;

FIG. 16 is a top plan view of the cap apparatus according to FIG. 14;

FIG. 17 is a sectional top view of the side seal of the cap apparatus, according to a preferred embodiment of the invention;

FIG. 18 is a sectional of the side seal of the cap apparatus according to an alternative preferred embodiment of the invention;

FIG. 19 is a sectional elevational view of the cap apparatus according to a preferred embodiment of the invention, shown in place upon a needle assembly;

FIG. 20 is a sectional of the side seal of the cap apparatus according to an alternative embodiment of the invention; and FIG. 21 is a side elevational view, partly in section, of a needle assembly according to a still further preferred embodiment of the invention;

FIG. 22 is an end elevational view of a needle retainer member, according to FIG. 21.

DETAILED DESCRIPTION OF THE INVENTION

While this invention is susceptible of embodiment in many different forms, there is shown in the drawings and will be shown in detail herein, several specific embodiments, with the understanding that the present disclosure is to be considered as an exemplification of the principles of the invention and is not intended to limit the invention to the embodiments illustrated.

A prior art syringe 15 is shown in partially exploded sectional view in FIG. 1. Syringe 15 is composed of syringe body 17, plunger assembly 19, needle assembly 21, and interchangeable, disposable ampoule 23.

Syringe body 15 is formed as a substantially hollow cylinder 25, having a substantially closed forward end 27 with coupling 29 having thread 31, and a substantially open rear end 33 with thread 35. In addition, a lateral aperture 37, bounded by front edge 39 and rear edge 41, is provided. Lateral aperture 37 has a width (not illustrated) which is sufficient to accommodate the width of ampoule 23, but has a length which is less than that of ampoule 23.

Ampoule 23, which has a conventional configuration, is composed of cylinder 43, which may be fabricated from glass, plastic or other substantially transparent, sterilizable material. Cylinder 43 has a substantially open rear end 45, and a necked front end 47, around which a collar 49, which may be of metal, is affixed. The forward face of collar 49 will have a central circular aperture 51. A puncturable seal 53, which may be formed from rubber, plastic or the like, is arranged underneath collar 49, and between collar 49 and necked front end 47, and centered relative to and spanning across the central circular aperture 51 in collar 49. Plunger piston 55 is arranged to fit, in a slightly forced manner, within cylinder 43 and seal off rear end 45 of cylinder 43. Plunger piston 55 is preferably fabricated from a sterilizable rubber material, or the like, which is capable of being pushed or pulled along the interior of cylinder 43 without losing its sealing integrity. To facilitate movement of plunger piston 55, a lubricant material may be disposed in circumferential grooves (not shown) around plunger piston 55, between plunger piston 55 and cylinder 43. Medicinal liquid 57 is sealed in ampoule 23 between seal 53 and plunger piston 55. The diameters of cylinder 25 and of cylinder 43 are such that ampoule 23 is capable of sliding or being propelled freely, once ampoule 23 is within cylinder 25.

Plunger assembly 19 is composed of outer collar 59, through which plunger shaft 61 is configured to freely slide. Outer collar 59 includes central well 63, on the inner surface of which are formed thread 65. Curved grip contour 67 is provided to facilitate grasping of syringe 15, for example, by the index and middle fingers of the operator, once syringe 15 has been assembled. Also surrounding plunger shaft 61 is helical spring 69 and inner collar 71. Inner collar 71 is configured to fit closely around plunger shaft 61 at inner flange 73. Inner collar 71 is also provided with a central well 75, and an inner ledge 77. The outer diameter of inner collar 71 is less than the inner diameter of central well 63 of outer collar 59. Disk 79 has a diameter greater than the inner diameter of inner flange 73, but less than the inner diameter of central well 75. Hook 81 is configured to be sufficiently sharp to be able to pierce into and engage plunger piston 55. To facilitate manipulation of plunger shaft 61, thumb ring 83 is provided, so that plunger shaft 61 may be pushed or pulled with only one-handed use by the operator.

Needle assembly 21 comprises a cap-like needle retainer member 85, which has thread 87 formed therein which mate with thread 31 of coupling 29. Hollow needle member 89 passes through needle retainer member 85 and includes exterior end 91 and interior end 93. Both exterior and interior ends 91 and 93, respectively, have sharp beveled points, for facilitating entry into the patient, and for piercing seal 53, respectively.

To assemble syringe 15, outer collar 59 is screwed onto thread 35 of syringe body 17. When fully attached, the forward flange 95 of curved grip contour 67 is positioned substantially immediately adjacent rear edge 41 of aperture 37. Needle assembly 21 is then screwed onto coupling 29. In its assembled unloaded resting position, for example, when syringe 15 is held with the exterior end 91 of needle member 89 pointing upward, inner flange 73 of inner collar 71 is approximately level with rear edge 41, and pusher disk 79 is at the bottom of central well 75, so that hook 81 is completely "below" rear edge 41. While the rear end 45 of ampoule 23 may be angled through aperture 37, and into contact with inner ledge 77 of inner collar 71, front edge 39 of aperture 37 prevents ampoule 23 from being fully inserted into syringe body 17. By pulling backward with thumb ring 83 on plunger shaft 61, against the force of spring 69, however, pusher disk 79 forces inner collar 71 to recede, permitting ampoule 23 to follow, and thus clear front edge 39 of aperture 37. When thumb ring 83 is released, spring 69 then forces inner collar 71 against rear end 45 of ampoule 23 forward toward forward end 27 of syringe body 17, and tending to force interior end 93 of needle member 89 against and through seal 53. The piercing process is completed when thumb ring 83 is pressed forward, with hook 81 piercing into, but preferably not through, plunger piston 55, and with pusher disk 79 pushing against plunger piston 55. An additional slight push on thumb ring 83 will then cause some of the liquid to be driven into needle member 89, and out exterior end 91, in the customary manner for preparing a syringe for positioning and injection.

The procedure for removal and exchange of the ampoule 23, after use, and the attendant potential problems, having already been described, they will be only briefly summarized here. Essentially, in the process of withdrawing plunger shaft 61, to bring it out from "within" ampoule 23, ampoule 23 will remain in its forward position within syringe body 25, even when plunger shaft 61 has been drawn back sufficiently to cause disk 79 to pull inner collar 71 away from ampoule 23. This is due to the gripping force seal 53 exerts upon interior needle end 93. The result is the necessity of the operator to use both hands in order to free the ampoule, which is undesirable with respect to efficiency and hygienic safety. An additional drawback of prior art syringe 15 is the need to use two hands in the removal of the used needle assembly which is also to be discarded, for the same reasons of hygienic safety and efficiency.

The improved syringe apparatus 101 of the present invention is shown in sectional view in FIG. 2, and in exploded view in FIG. 3. Syringe 101, which is configured to utilize the same conventional ampoule 23 as previously described, includes syringe body 103, plunger assembly 105, and needle assembly 107. The components of ampoule 23, having the same configuration as discussed with respect to the prior art syringe construction, will be referred to with the same, previously-used reference numbers.

Syringe body 103 includes cylindrical cage 109, having forward end 111 with narrowed coupling 113, and rearward end 115 with thread 117. In order to save on material and lighten the weight, cylindrical cage 109 may be configured with mostly open-sided walls, as shown. Syringe body 103 also includes lateral aperture 119, which is bounded by front edge 121 and rear edge 123, and has a width sufficient to accommodate ampoule 23. Plunger assembly 105 includes plunger shaft 125, thumb ring 127, outer collar 129, finger grip collar 131, helical springs 133, pusher disk 135, and ampoule carrier frame 137. Hook 139 is affixed to pusher disk 135. Ampoule carrier frame 137 includes stem 141, central well 142, body 143, spring retainer 144, and needle ejector projection 147. Body 143 has an internal diameter which is greater than the outer diameter of ampoule 23, and has a lateral aperture 149 having front edge 151 and rear edge 153, which are spaced sufficiently apart to permit the ready insertion or release of ampoule 23, when ampoule carrier frame 137 is appropriately aligned in syringe body 103, so that ampoule 23 will be substantially surrounded by ampoule carrier frame 137, at least with respect to both rear end 45 and front end 47 of ampoule 23. Notch 167 (FIG. 3) extends forward from front edge 151 to forward notch edge 168. Body 143 also has an external diameter which is less than the internal diameter of syringe body 103, so as to enable ampoule carrier frame 137 to move forward and backward within syringe body 103.

Needle assembly 107 includes needle retainer member 155, which, in the preferred embodiment shown in FIGS. 2–5, has a substantially smooth interior surface. Needle member 157 passes through needle retainer member 155, and has substantially the same configuration as needle member 89 previously described, with exterior end 159 and interior end 161.

When syringe 101 is assembled, and held in an unloaded, resting position, for example, with exterior end 159 of needle member 157 held upright, and with no pressure being exerted on plunger shaft 125, and no ampoule 23 loaded, ampoule carrier frame 137 is biased into an intermediate position, relative to syringe body 103, by spring 133, such that while rear end 45 of ampoule 23 may be inserted through aperture 119, and through aperture 149, to come into contact with rear wall 163 of ampoule carrier frame 137, front end 47 of ampoule 23 cannot clear the front edges 121, 151 of apertures 119, and 149, respectively. Upon pulling rearward on thumb ring 127, however, ampoule carrier frame 137 is drawn backward, against the bias of spring 133, and ampoule 23 is capable of clearing front edge 121 of aperture 119. It is necessary that in the above-described resting position of ampoule carrier frame 137, front edge 151 is not aligned with, but rather is forward of, front edge 121. Otherwise, when plunger shaft 125 is drawn backward, front edge 151 would move rearward relative to front edge 121, and ampoule 23 would still be prevented from being fully inserted into body 143.

Upon release of plunger shaft 125, spring 133 pushes ampoule carrier frame 137 forward, causing seal 53 of ampoule 23 to contact, and be pierced by, interior end 161 of needle member 157. Rear wall 163 of ampoule carrier frame 137 then moves forward to a position slightly rearward of the position it occupied when syringe 101 is in its unloaded configuration. The injection procedure is then executed.

Removal of ampoule 23 is accomplished by drawing backward on plunger shaft 125 with thumb ring 127, in the manner previously described. However, ampoule 23 is not provided with an opportunity to "hang up" on interior end 161 of needle member 157, since, as plunger shaft 125 is drawn back, pusher disk 135 abuts rear wall 163 of ampoule carrier frame 137, and begins to drive ampoule carrier frame 137 backward, toward the ampoule insertion position. Since ampoule carrier frame 137 completely surrounds ampoule 23, the inner front wall 165 of ampoule carrier frame 137 pushes against collar 49 of ampoule 23, and drives ampoule 23 off of interior end 161 of needle member 157. Since the rearward movement of ampoule carrier frame 137 is controlled by pusher disk 135, whether hook 139 maintains a grip on plunger piston 55 has no effect on the removal procedure. Once ampoule 23 has been freed from interior needle end 161, and plunger shaft 125 has been fully withdrawn from within ampoule 23, ampoule 23 is free to slide within body 143 of ampoule carrier frame 137, and upon alignment of front edge 151 with front edge 121, the operator may simply turn syringe 101 over in his hand, can drop the spent ampoule into an appropriate waste receptacle.

An additional advantageous feature of the improved syringe 101 of the present invention is the provision of a mechanism for the selective automatic ejection of the used, disposable needle assembly. With the current concerns regarding the possible transmission of disease via syringe needles, it is especially desirable to provide a method of separating and ejecting a needle assembly from a syringe body without the operator having to directly handle the now-potentially contaminated used needle assembly.

As previously mentioned, ampoule carrier frame 137 is provided with a notch 167, which, in the embodiment shown in FIGS. 2–5, extends from the forward edge 151 of lateral aperture 149, to forward notch edge 168. A corresponding axially extending projection 169 emanates from the inner front wall 171 of syringe body 103. When syringe apparatus 101 is assembled, notch 167 and projection 169 must be aligned. When an ampoule 23 is installed in ampoule carrier frame 137, ampoule 23 is held in its forwardmost position within ampoule carrier frame 137, against the inside front surface 138. Collar 49 of ampoule 23 abuts rear edge 170 of projection 169, and ampoule carrier frame 137 is prevented from moving forward to its forwardmost possible position. Accordingly, needle ejector projection 147 is positioned rearwardly away from needle retainer member 155. When pressure is applied to thumb ring 127, to force plunger piston 55 forward, the force is transmitted through plunger piston 55 and into the liquid 57. Part of this force is transferred to collar 49 and against the rear edge 170 of projection 169. At no time when an ampoule 23 is in ampoule carrier frame 137 can any thrusting force from plunger shaft 125 be transferred to ampoule carrier frame 137, and so ampoule carrier frame 137 is prevented from being moved forward.

When the operator is finished with the injection procedures, the ampoule may be removed, one-handed, using the process and apparatus described, and the needle assembly ejected in the following manner. When there is no ampoule 23 in ampoule carrier frame 137, the operator may simply press forward on thumb ring 127 until thumb ring collar 122 abuts front surface 141 of ampoule carrier frame 137. The force is thus directly transferred to ampoule carrier frame 137, which is then free to move forward, with needle ejector projection 147 pushing needle retainer member 155 off of coupling 113. While the preferred embodiment shown employs one notch 167 and one projection 169, the alignment feature may effectively employ a greater number of corresponding notches and projections.

In the embodiment shown in FIGS. 2–5, coupling 113 is shown as being a substantially cylindrical projection, having a substantially smooth outer surface, while needle retainer member 155 has a substantially cylindrical, substantially smooth inner surface, such that needle retainer member 155 is held on coupling 113, once mounted, by the simple friction between the respective inner and outer surfaces. Needle retainer member 155 may also be provided with a circumferentially extending groove 156, the function of which will be described hereinafter. Alternative configurations of needle ejector projection, coupling and needle retainer member may be desired, as indicated by FIGS. 6–12.

In FIG. 6, for example, needle retainer member 181 may be provided with one or more rearwardly extending, flexible prongs 183, which are configured to fit around and grasp coupling 185, by fitting into notches 187. Upon exertion of pushing force by needle ejector projection 189, prongs 183 will yield, spreading apart sufficiently to allow needle retainer member 181 to be ejected. Needle retainer member 181 also may be provided with a circumferentially extending groove 182, for retaining a cap, as described hereinafter. In FIG. 9, a substantially flat variant of this configuration is provided, in which needle retainer member 201 is formed as a substantially C-shaped clip, having arms 203, and a central core 205, which supports needle member 207. Arms 203 are provided with hooks 209 which will engage notches 211 in the slots 213 in the coupling 215. Ejection is accomplished when needle ejector projection 217 pushes on core 205 whereupon body of projection 217 will force arms 203 to yield and bend outwardly as previously described and projection 217 will abut core 205 and release needle 207.

The needle retainer member 191 of FIG. 7 is also provided with one or more rearwardly projecting prongs 193. Prongs 193 are provided to fit into forward facing notches 195 in the forward end 197 of syringe body 199. Prongs 193 may be beveled to facilitate movement in and out of notches 195. The needle retainer member 191 is shown including threads or raised edges on its inner surface which will interlock with corresponding threads or raised edges on the outer surface of coupling 192 when member 191 is joined with coupling 192. When the carrier frame 188 is pushed forward projection 198 will contact retainer member 191 allowing it to be ejected. Retaining member 191 is further shown including a notch 191a which permits member 191 to expand allowing it to be easily positioned on coupling 192.

In FIG. 8, two rearwardly projecting barbed prongs 194 on needle retainer member 190 are configured to be received by apertures 196. Prongs 194 have beveled and are biased to project slightly radially inwardly, and must be spread outwardly slightly in order to install needle retainer member 190 onto syringe body 186. When needle retainer member 190 is pushed forward prongs 194 will bend outward and yield, and projection 198 will eject retainer member 190.

Rather than by forcing inwardly biased arms outward, ejection can be accomplished by forcing outwardly biased arms inward, as shown in FIGS. 11 and 12. In FIG. 11, a needle retainer member 221 has two rearwardly projecting prongs 223, with outwardly directed barbs 225. Needle retainer member 221 is configured to fit through opening 229 in coupling 227, grasping behind the opening with barbs 225. Opening 229 has a forward-facing concave surface which forces prongs 223 together, to cause barbs 225 to pass opening 229. Once barbs 225 have passed the opening 229, prongs 223 are free to spread slightly, and barbs 225 prevent needle retainer member 221 from being removed or falling out. Needle ejector projection 231 is a forward-facing concave surface which, when needle ejector projection 231 is brought into contact with prongs 223, forces barbs 225 toward each other, to release opening 229, and permit ejection of needle retainer member 221. Needle retainer member may also be provided with a circumferential groove 222.

The configuration of FIG. 12 is slightly different, in that needle retainer members 241 and 243 are both configured as substantially flat, rectangular members, both having outwardly-biased, rearwardly-projecting prongs 245 and 247, respectively. Either is configured to fit through opening 249 in coupling 251, grasping behind the opening with barbs 253 or 255, respectively. Needle ejector projection 257, again, is a forward-facing concave surface which forces prongs 245 or 247 together, to cause barbs 253 or 255 to release opening 249 and permit ejection of the respective needle retainer member 241 or 243.

Each of the foregoing configurations is intended to be utilized with the notches and projections of the previously discussed ejection prevention mechanism, the details of which have been omitted from FIGS. 6–9, and 11, 12, for clarity.

A further alternative needle assembly ejection system is disclosed in FIG. 10. Needle retainer member 261 is a cap-like member, having a large internal space 263, and an opening 265, which has a smaller diameter than that of internal space 263. Needle ejector projection 267 is formed as two or more spread, flared projection members 269, which are normally biased outwardly, and are shown in their configuration, when the ampoule carrier frame is in a forward position. Needle retainer member 261 is pressed upon projection members 269 which, due to their forward tapering surfaces 271, are forced toward each other. Opening 265 passes ridges 273 on projection members 269, which are then permitted to spread apart to a slight degree, holding needle retainer member 261 against coupling 275. Ejection is accomplished, by continued pushing of plunger shaft 125 by thumb ring 127, after the injection is completed, which causes ampoule carrier frame 269 to move forward, forcing projection members 269 to move toward one another causing needle retainer member 261 to simply fall off of syringe body 103.

A still further alternative needle assembly is shown in FIGS. 21 and 22. In FIG. 21, a needle retainer member 421 has two rearwardly projecting prongs 423. Each of prongs 423 has a flat inner surface 425, and an arcuate outer surface 427, as shown in FIG. 22. Needle retainer member 421 is configured to fit through opening 429 in coupling 426, grasping behind the opening with semicircumferential grooves 428. Arcuate outer surfaces 427 of prongs 423 converge rearwardly, so that prongs 423 are pressed together by the inner edge of opening 429. Once prongs 423 have passed the opening 429, prongs 423 are free to spread slightly, and the inner edge of opening 429 prevents needle retainer member 421 from being removed or falling out. Needle ejector projection 431 is a forward-facing concave surface which, when needle ejector projection 431 is brought into contact with prongs 423, forces then toward each other, to enable grooves 428 to release the inner edge of opening 429, and permit ejection of needle retainer member 421.

Still another feature of the present invention is the provision of an improved cap apparatus for covering the needle assembly. It is desirable to cover the needle assembly with a cap, prior to mounting on the syringe body, to prevent injury, and to preserve the needle in a sterilized condition. It is also desirably to cover the needle tip after usage, in order to prevent injury and possible exposure to contamination or disease. Prior art cap apparatus comprised a simple cap member which must be positioned by approaching the needle member and needle retainer member in a motion directly toward the exposed needle tip, which is an undesirable potentially hazardous movement. The improved cap apparatus of the present invention is shown in several embodiments in FIGS. 13–19. Cap apparatus 301 is constructed as a substantially conical, rounded member 302 having a longitudinally extending slit 303, preferably running from rear edge 304 to cap point 305. Tabs 307 emanate from member 302 on the side of member 302 symmetrically about a position substantially opposite slit 303. Member 302, in a preferred embodiment of the invention, is fabricated from a strong, but substantially flexible material, such as a plastic. Tabs 307 are configured to be substantially rigid, relative to their connections to member 302, so that by the exertion of pressure to force tabs 307 toward each other, as seen in FIGS. 14 and 16, member 302 spreads open along slit 303. The opening 308 is advantageously configured to be wide enough so that cap 301 may be positioned over a needle assembly, such as needle assembly 315 (FIG. 19) from the side (arrow A), rather than from the direction that the needle tip 316 points (arrow B). Once cap apparatus 301 is in position, tabs 307 are released, and opening 308 closes, and member 302 grasps and fits around needle assembly 315. In order to assist cap apparatus 301 in maintaining its position upon needle assembly 315, member 302 may have an inwardly projecting circumferentially extending ridge 309, which is configured to mate with a circumferentially extending groove 317 on needle retainer member 318 (or groove 156 of needle retainer member 155, groove 182 of needle retainer member 181, or groove 222 of needle retainer member 221 of the previous embodiments).

Member 302 may be provided with a reinforcement, to bias it toward a closed position. Such reinforcement may take the form of a light spring metal or thickened plastic member 310 (FIG. 15) positioned on the inside, or outside, of member 302, substantially in the region of attachment of tabs 307, which is biased to tend to bring the edges of slit 303 toward one another.

The portions of member 302 which form the edges of slit 303 may also be advantageously configured to help keep cap apparatus 301 closed and in position upon needle assembly 315, in the absence of a conscious effort of the operator to remove the cap apparatus 301. For example, edges 311 and 312 of a member 302, forming a slit 303, may comprise a mating ridge and groove combination, respectively. (FIG. 17) In an alternative embodiment, edges 319 and 320 may have overlapping and interlocking ridges 321 and 322, and grooves 323 and 324, respectively, which will hold slit 303 closed, until overcome by the pressure exerted upon tabs 307. (FIG. 18) Alternatively, as shown in FIG. 20, cap 341 may include a preformed weakened area 343 along a predetermined line extending from the tip of cap 301 to its base whereupon the force exerted by the user on tabs 307 will break the cap along the weakened line to form slit 303.

The foregoing description and drawings merely explain and illustrate the invention, and the invention is not limited thereto except insofar and the appended claims are so limited, as those skilled in the art who have the disclosure before them will be able to made modifications and variations therein without departing from the scope of the invention.

What is claimed is:

1. A syringe apparatus, of the type having a syringe body having a forward end and a rearward end thereof, and a plunger member operably associated with the syringe body and operably configured for longitudinal movement relative to the syringe body, said syringe apparatus comprising:

a needle retainer member, operably configured to be releasably affixed onto a portion of said forward end of said syringe body;

means for releasably affixing said needle retainer member upon said forward end of said syringe body, and for enabling ejection of said needle retainer member off of said syringe body through extension of force upon said needle retainer member, parallel to said longitudinal axis, in a direction away from said syringe body, operably associated with said needle retainer member and said syringe body; and means for ejecting said needle retainer member off of said syringe body, operably associated with said needle retainer member and said plunger member, said means for ejection said needle retainer member being actuated only upon actuation of said plunger member.

2. A syringe apparatus, according to claim 1, wherein said means for releasably affixing said needle retainer member upon said forward end of said syringe body comprises:

at least one resilient grasping member operably disposed upon a rearward portion of said needle retainer member; and means for releasably engaging said at least one grasping member, operably disposed upon said forward end of said syringe body, such that when said needle retainer member is brought into juxtaposition against said forward end of said syringe body, said at least one resilient grasping member grasps said syringe body to maintain said needle retainer member in operable engagement with said syringe body, and whereupon exertion of a predetermined force against said needle retainer member, said at least one grasping member and said means for releasably engaging said at least one grasping member cooperate to enable ejection of said needle retainer member from said syringe body.

3. A syringe apparatus, according to claim 2, wherein said at least one resilient grasping member comprises:
   a prong member extending rearwardly from said needle retainer member; and
   at least one barb member projecting inwardly from said prong member.

4. A syringe apparatus, according to claim 3, wherein said means for engaging said at least one grasping member, operably disposed upon said forward end of said syringe body comprises:
   at least one recess in said forward end of said syringe body, operably configured to receive at least one of said at least one prong member and said at least one barb member.

5. A syringe apparatus, according to claim 2, wherein said at least one resilient grasping member comprises:
   a resilient prong member extending rearwardly from said needle retainer member; and
   at least one barb member projecting outwardly from said prong member.

6. A syringe apparatus, according to claim 5, wherein said means for engaging said at least one grasping member, operably disposed upon said forward end of said syringe body comprises:
   at least one recess in said forward end of said syringe body, operably configured to receive at least one of said at least one prong member and said at least one barb member.

7. A syringe apparatus, according to claim 1, wherein said means for releasably affixing said needle retainer member upon said forward end of said syringe body comprises:
   at least one resilient grasping member operably associated with said syringe body, and operably positioned adjacent said forward portion thereof; and
   means for releasably engaging said at least one grasping member, operably disposed upon said needle retainer member, such that when said needle retainer member is brought into juxtaposition against said forward end of said syringe body, said at least one resilient grasping member grasps said needle retainer member to maintain said needle retainer member in operable engagement with said syringe body, and
   whereupon exertion of a predetermined force against said needle retainer member, said at least one grasping member and said means for releasably engaging said at least one grasping member cooperate to enable ejection of said needle retainer member from said syringe body.

8. A syringe apparatus, according to claim 2, wherein said needle retainer member includes an inner recess having an inner surface and a rearwardly facing opening therein, and said at least one resilient grasping member comprises:
   at least one circumferentially extending ridge emanating radially inwardly from said inner surface of said inner recess.

9. A syringe apparatus, according to claim 8, wherein said means for engaging said at least one grasping member, operably disposed upon said forward end of said syringe body comprises:
   at least one circumferentially extending recess in said forward end of said syringe body, operably configured to receive said at least one circumferentially extending ridge emanating radially inwardly from said inner surface of said inner recess.

* * * * *